United States Patent
Bates et al.

(10) Patent No.: US 7,563,272 B2
(45) Date of Patent: *Jul. 21, 2009

(54) EMBOLI FILTRATION SYSTEM AND METHODS OF USE

(75) Inventors: Mark C. Bates, Charleston, WV (US); Michael Hogenduk, Palo Alto, CA (US); Nicola A. Pisano, Rancho Santa Fe, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 791 days.

This patent is subject to a terminal disclaimer.

(21) Appl. No.: 11/037,881

(22) Filed: Jan. 18, 2005

(65) Prior Publication Data
US 2005/0125023 A1  Jun. 9, 2005

Related U.S. Application Data

(63) Continuation of application No. 10/278,172, filed on Oct. 21, 2002, now abandoned, which is a continuation-in-part of application No. 09/774,197, filed on Jan. 29, 2001, now Pat. No. 6,468,291, which is a continuation-in-part of application No. 09/354,897, filed on Jul. 16, 1999, now Pat. No. 6,179,859.

(51) Int. Cl.
*A61F 2/01* (2006.01)
(52) U.S. Cl. .................................................. 606/200
(58) Field of Classification Search .................. None
See application file for complete search history.

(56) References Cited

U.S. PATENT DOCUMENTS

| | | |
|---|---|---|
| 3,472,230 A | 10/1969 | Fogarty |
| 3,592,186 A | 7/1971 | Oster |
| 3,683,904 A | 8/1972 | Forster |
| 3,889,657 A | 6/1975 | Baumgarten |
| 3,952,747 A | 4/1976 | Kimmell, Jr. |
| 3,996,938 A | 12/1976 | Clark, III |

(Continued)

FOREIGN PATENT DOCUMENTS

DE   28 21 048   7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Tuan V Nguyen
(74) *Attorney, Agent, or Firm*—Crompton, Seager & Tufte LLC

(57) ABSTRACT

An emboli filtration apparatus is provided comprising a guide wire having a filter element captured thereon, so that the guide wire is free to rotate and translate while the filter element remains stationary. The apparatus allows for movement and rotation of the guide wire as devices are advanced over it to treat occlusive disease, substantially without dislodging the filter element. In a preferred embodiment, the guide wire comprises a proximal stop configured to reposition the filter element during a medical procedure without having to remove or insert additional interventional devices.

9 Claims, 7 Drawing Sheets

U.S. PATENT DOCUMENTS

| | | |
|---|---|---|
| 4,046,150 A | 9/1977 | Schwartz et al. |
| 4,425,908 A | 1/1984 | Simon |
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,886,061 A | 12/1989 | Fischell et al. |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Giffort, III et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazarus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vowerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,807,398 A | 9/1998 | Shaknovich |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |

| | | | |
|---|---|---|---|
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,661 B1 | 1/2001 | Khosravi et al. |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,325,815 B1 * | 12/2001 | Kusleika et al. ............ 606/200 |
| 6,336,934 B1 * | 1/2002 | Gilson et al. ................ 606/200 |
| 6,344,049 B1 | 2/2002 | Levinson et al. |
| 6,346,116 B1 | 2/2002 | Brooks et al. |
| 6,355,057 B1 | 3/2002 | DeMarais et al. |
| 6,361,546 B1 | 3/2002 | Khosravi |
| 6,371,971 B1 * | 4/2002 | Tsugita et al. .............. 606/200 |
| 6,432,122 B1 | 8/2002 | Gilson et al. |
| 6,468,291 B2 | 10/2002 | Bates et al. |
| 6,843,798 B2 * | 1/2005 | Kusleika et al. ............ 606/200 |
| 7,491,216 B2 * | 2/2009 | Brady ........................ 606/200 |
| 2002/0002384 A1 | 1/2002 | Gilson et al. |
| 2002/0052626 A1 | 5/2002 | Gilson et al. |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 | 3/1993 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 | 10/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/04875 A1 | 2/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |

| | | |
|---|---|---|
| WO | WO 98/51237 | 11/1998 |
| WO | WO 98/55175 | 12/1998 |
| WO | WO 99/09895 | 3/1999 |
| WO | WO 99/16382 | 4/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprothesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993 ).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

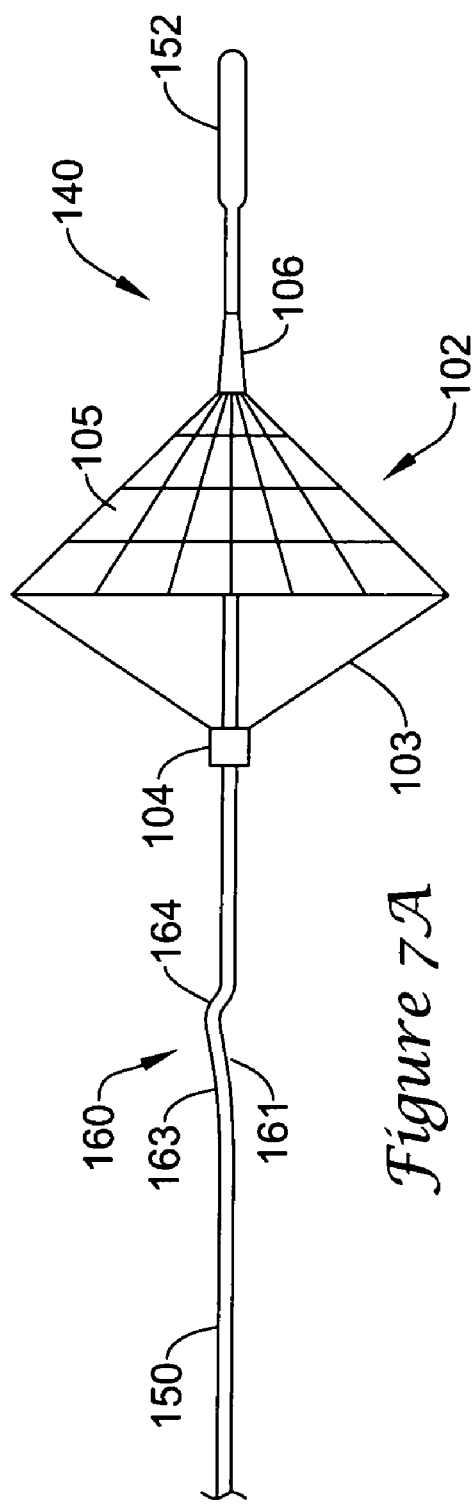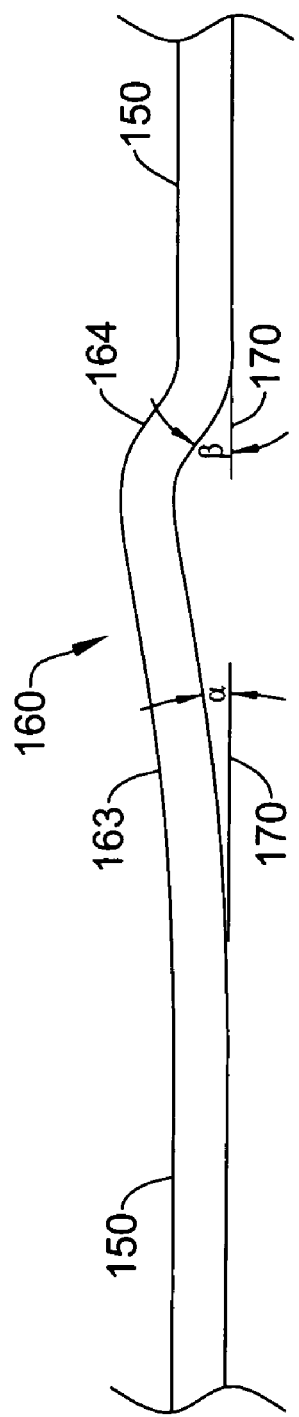
Figure 7A
Figure 7B

EMBOLI FILTRATION SYSTEM AND METHODS OF USE

REFERENCE TO RELATED APPLICATIONS

This application is a continuation application of application Ser. No. 10/278,172 filed on Oct. 21, 2002 now abandoned, which in turn is a continuation-in-part of application Ser. No. 09/774,197 filed on Jan. 29, 2001, now U.S. Pat. No. 6,468,291, which in turn is a continuation-in-part of application Ser. No. 09/354,897 filed on Jul. 16, 1999, now U.S. Pat. No. 6,179,859.

FIELD OF THE INVENTION

The present invention relates to apparatus and methods for removing emboli from the blood stream that are generated during treatment of vascular disease, such as angioplasty, atherectomy or stenting. More particularly, an emboli filtration device and methods are provided having a captured filter that enables movement of a guide wire associated with the filter without displacing the filter.

BACKGROUND OF THE INVENTION

Atherosclerosis and other vascular occlusive diseases are becoming prevalent today in many developed countries. In such diseases, the flow areas of blood vessels become narrowed or occluded by the buildup of plaque on the walls of the vessels, leading to ischemia, and depending upon the location of the vessel, damage to the organ or limb. A number of surgical and percutaneous procedures have been developed for treating stenosis in the coronary arteries and carotid arteries, including endarterectomy, angioplasty, atherectomy and stenting.

One problem frequently encountered during such procedures is that pieces of plaque ("emboli") often are dislodged from the stenosis or the vessel wall. Such emboli may travel into smaller diameter regions of the vasculature, blocking blood vessels and causing ischemic injury. This problem is especially severe where the emboli are permitted to travel into the coronary arteries and carotid arteries, and can result in infarction, stroke and even death.

Emboli filtration devices are known in which filter elements are deployed against the walls of a vessel distal of a stenosis. Such filters typically comprise a polymer or wire sac mounted on a distal region of a guide wire or angioplasty catheter, and permit blood to flow through the filter while trapping emboli. Once treatment of the stenosis is completed, the filter containing the captured emboli is contracted and withdrawn from the vessel.

For example, U.S. Pat. No. 5,814,064 to Daniel et al. (Daniel) describes an emboli capturing system having a radially expandable mesh filter disposed on the distal end of a guide wire. The filter is deployed distal of a region of stenosis, and any interventional devices, such as an angioplasty balloon or stent delivery system are advanced along the guide wire. The filter is designed to capture emboli generated during treatment of the stenosis while permitting blood to flow through the filter.

U.S. Pat. No. 4,723,549 to Wholey et al. (Wholey) describes an angioplasty catheter having a filter element disposed on its distal end. The filter is supported on a plurality of circumferential struts, and is expanded against an interior wall of a vessel, distal of a stenosis, by an inflation balloon. An angioplasty balloon is disposed on the catheter proximal of the filter for dilating the stenosis. The filter captures emboli dislodged during the dilatation procedure, and then is contracted and removed from the vessel with the angioplasty catheter.

A key disadvantage of previously known emboli filtration systems, such as described in the foregoing patents, is that the filters in those devices are fixedly attached to the guide wire or angioplasty catheter, respectively. If the catheter or guide wire is rotated, bumped or moved after the filter has been deployed, there is a substantial risk that the filter will become temporarily dislodged or skewed, thereby permitting emboli to escape past the filter. Such motion is especially likely to occur when other devices such as an angioplasty balloon catheter are deployed along the guide wire after the filter is deployed, as in the Daniel patent.

U.S. Pat. No. 6,336,934 to Gilson et al. (Gilson) describes an embolic protection device having a collapsible filter element that is mounted on a tubular sleeve, wherein the tubular sleeve is slidable and rotatable on a guide wire between proximal and distal stops. The filter element on the tubular sleeve is delivered in a collapsed state within a catheter and self-deploys when the catheter is retracted. In the deployed state, the tubular sleeve facilitates some manipulation of the guide wire while potentially reducing disruption of the filter element.

One drawback associated with the device described in the Gilson patent is that the guide wire is delivered into the patient's vessel with the filter element disposed in a collapsed state between the proximal and distal stops near the distal end of the guide wire. The placement of the filter element near the distal end of the guide wire during delivery may make it difficult for the guide wire to negotiate tortuous anatomy during delivery. It would be advantageous to deliver the guide wire in an unencumbered manner to the site of the occlusion, then subsequently deliver other interventional devices including the filter element.

In view of these drawbacks of previously known devices, it would be desirable to provide emboli filtration apparatus and methods having a filter element that remains stationary once deployed.

It also would be desirable to provide emboli filtration apparatus and methods having a filter that may be deployed along a guide wire, but is configured so that subsequent displacements or rotation of the guide wire will not dislodge the filter.

It further would be desirable to provide emboli filtration apparatus and methods that reduce the risk of emboli escaping from a filter element.

It still further would be desirable to provide emboli filtration apparatus and methods that reduce the risk of trauma to vessel endothelium resulting from movement transferred to the emboli filtration apparatus.

It still further would be desirable to provide emboli filtration apparatus and methods that enable a filter element to be repositioned during a medical procedure without having to remove or insert additional interventional devices.

SUMMARY OF THE INVENTION

In view of the foregoing, it is an object of the present invention to provide emboli filtration apparatus and methods having a filter element that remains stationary once deployed.

It is another object of the present invention to provide emboli filtration apparatus and methods having a filter that may be deployed along a guide wire, but is configured so that subsequent displacements or rotation of the guide wire will not dislodge the filter.

It is also an object of this invention to provide emboli filtration apparatus and methods that reduce the risk of emboli escaping from a filter element.

It is a further object of the present invention to provide emboli filtration apparatus and methods that reduce the risk of trauma to vessel endothelium resulting from movement transferred to the emboli filtration apparatus.

It is still a further object of the present invention to provide emboli filtration apparatus and methods that enable a filter element to be repositioned during a medical procedure without having to remove or insert additional interventional devices.

These and other objects of the present invention are accomplished by providing emboli filtration apparatus comprising a guide wire having a filter element captured thereon, so that the guide wire is free to rotate and translate while the filter element remains stationary. The apparatus thus allows for movement and rotation of the guide wire as devices are advanced over it to treat a stenosis, substantially without dislodging the filter element. Accordingly, the risk of permitting emboli to escape during temporary displacement or skewing of the filter element is reduced, as well as movement-induced trauma of the vessel endothelium.

In a preferred embodiment, the apparatus comprises a guide wire having a filter element captured for rotation and translation on a distal end thereof. The filter element preferably comprises a wire or polymer sac affixed to a plurality of self-expanding struts. The filter element has a contracted state, suitable for transluminal insertion disposed inside a retractable sheath, and a deployed state, wherein an outer perimeter of the filter element engages the walls of a vessel when the sheath is retracted proximally.

The filter element includes a proximal capture ring having a diameter that is larger than the diameter of the guide wire, but smaller than the diameter of the distal tip of the guide wire. The capture ring allows the guide wire to move freely relative to the filter element over a limited range, so that movement or rotation of the guide wire does not cause the filter to move or to scrape against the walls of the vessel. When it is desired to retract the filter element, the guide wire is pulled proximally so that the distal tip of the guide wire engages the capture ring and pulls the filter element back into a sheath to its contracted state.

Optionally, the filter element may include a cylindrical sleeve that ensures that the filter forms an adequate seal against the walls of the vessel in the deployed state, thus preventing bypass flow around the filter. The sleeve also assists in orienting the axis of the filter element parallel to the axis of the vessel.

In a further alternative embodiment of the present invention, the guide wire further comprises a proximal stop disposed proximal of the distal tip. The proximal stop is configured so that a filter element having an elastomeric capture ring may be advanced distally over the proximal stop during delivery of the filter element and locked distal of the proximal stop. As a further alternative, the proximal stop may be configured to permit the capture ring to pass distally over it, but prevent proximal passage.

During a medical procedure, the filter element is advanced to a central position between the proximal stop and distal tip. Advantageously, if it becomes necessary to advance the filter element distally during the medical procedure, the guide wire may be advanced distally to cause the proximal stop to abut the capture ring and urge the filter element distally. Using the proximal stop of the guide wire, it is not necessary to remove interventional devices or insert a push tube over the guide wire to reposition the filter element.

Methods of using the apparatus of the present invention to remove emboli during a surgical or percutaneous transluminal procedure also are provided.

BRIEF DESCRIPTION OF THE DRAWINGS

Further features of the invention, its nature and various advantages will be apparent from the accompanying drawings and the following detailed description of the preferred embodiments, in which:

FIGS. 7A-7B are side views of a further alternative embodiment of a proximal stop provided in accordance with principles of the present invention.

DETAILED DESCRIPTION OF THE INVENTION

The present invention is directed to an emboli filtration system and methods that filter out emboli generated during surgical or percutaneous interventional procedures. In accordance with the principles of the present invention, a filter element is captured on a guide wire so that the guide wire is capable of rotation and translation, without disturbing the placement of the filter element. Because the filter element is captured on the guide wire, however, the filter element is readily removed by retracting the guide wire into a sheath.

Figure 1:
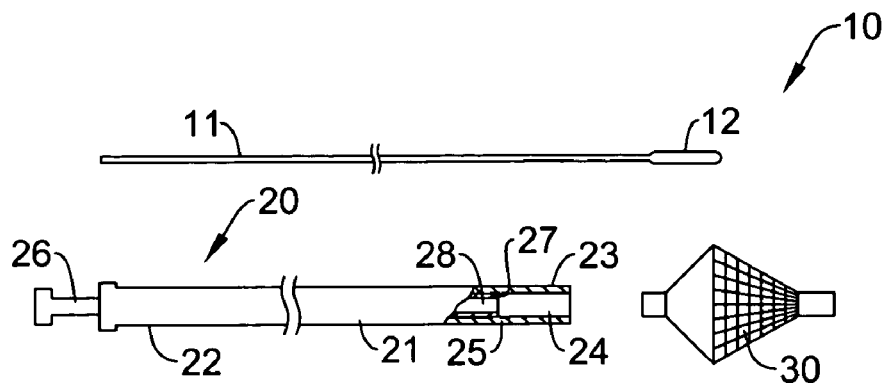
FIG. 1 is a side view of the components of a first embodiment of apparatus constructed in accordance with the principles of the present invention.

Referring to FIG. 1, apparatus 10 of a first embodiment of the present invention comprises guide wire 11, delivery sheath 20 and filter element 30. In accordance with the principles of the present invention, guide wire 11 includes enlarged diameter distal region 12. Guide wire 11 may be constructed of material commonly used in guide wire construction, such as stainless steel or a high strength polymer. Distal region 12, which acts as a distal stop to limit travel of filter element 30 in the distal direction, comprises a soft metal or metal alloy coil or may be formed from a flexible polymer, such as polyethylene or nylon, molded onto the distal region of the guide wire. Alternatively, guide wire 11 and distal region 12 may comprise a mechanism, such as are known in the art, for steering distal region 12 through a patient's vasculature. Illustratively, guide wire 11 may have a diameter of about 0.018 inches (0.46 mm) and the diameter of distal region 12 may be about 0.022 inches (0.56 mm).

Delivery sheath 20 comprises flexible catheter 21 having proximal end 22, distal end 23, and interior lumen 24. Push tube 25 is disposed within lumen 24, and includes proximal end 26, distal end 27 and guide wire lumen 28, to permit catheter 21 and push tube 25 to be advanced along guide wire 11. Proximal end 26 of push tube 25 extends through proximal end 22 of catheter 21, so that push tube 25 may be translated in the distal and proximal directions relative to catheter 21. Catheter 21 and push tube 25 preferably comprise flexible materials such as are commonly used in catheter construction, for example, polyethylene, polyurethane or nylon. Delivery sheath 20 preferably has an outer diameter of about 4 Fr.

Figure 2A:
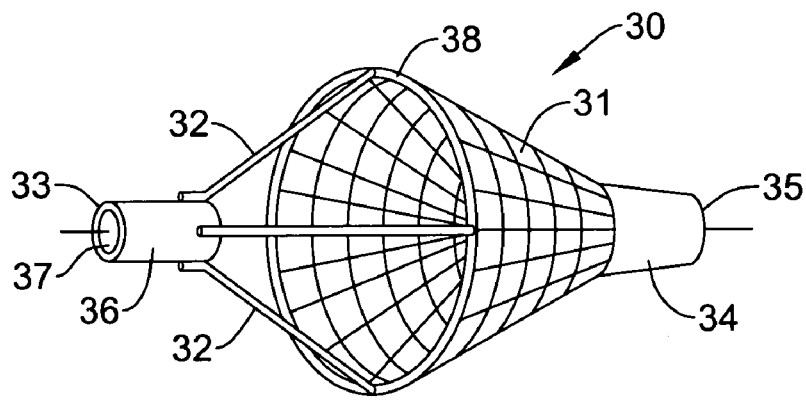
FIGS. 2A-2B are, respectively, a perspective view and end view of the filter element of FIG. 1.
Figure 2B:
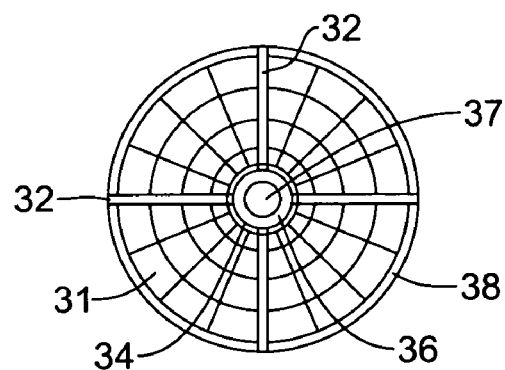

Referring now to FIGS. 2A and 2B, filter element 30 comprises funnel-shaped filter sac 31 coupled to plurality of self-expanding struts 32 at proximal end 33 and soft elastomeric cone 34 at distal end 35. Struts 32 are affixed to capture ring 36, and self-expand from a contracted state, when filter element is disposed in lumen 24 of catheter 21, and a deployed state, when filter element is ejected from delivery sheath 20. In the deployed state, struts 32 extend outward to urge the perimeter of sac 31 into engagement with the walls of a vessel.

Struts 32 may comprise a resilient metal or metal alloy, such as stainless steel or nickel-titanium, or a resilient polymer. It is expected that at least three struts 32 spaced equidistant apart around the perimeter of sac 31 should be employed to provide adequate expansion and control of the sac, although a greater number may be used. Alternatively, struts 31 may comprise flexible strands, and expansion of sac 31 may be accomplished by adding a flexible and resilient self-expanding nickel-titanium hoop along perimeter 38 of the sac.

Particulate matter, such as emboli, pass through struts 32 and are trapped against sac 31, which permits blood to pass freely through. The size of emboli trapped by sac 31 is determined by the pore size of the sac, and preferably is about 0.0012 inches (30 microns). Sac 31 may comprise a polymer sleeve affixed to struts 32 or a self-expanding wire mesh constructed from a resilient metal alloy, for example, nickel-titanium.

Capture ring 36 has bore 37 with an inner diameter greater than the diameter of guide wire 11, but smaller than the diameter of distal region 12. This allows guide wire 11 to be rotated or translated distally relative to filter element 30, without imposing a force on the filter element that might temporarily dislodge the filter element. Accordingly, various devices, such as angioplasty catheters, atherectomy devices or stent delivery systems may be exchanged on guide wire 11 without disturbing filter element 30 or causing it to scrape against the walls of the vessel. As will of course be understood, capture ring 36 need not be a tubular member, but may have any suitable shape that allows guide wire 11 to pass freely through it.

Elastomeric cone 34 is coupled to the distal end of sac 31 and includes a tapered central lumen that permits guide wire 11 to freely pass through cone 34 with minimal clearance. Elastomeric cone 34 preferably comprises a non-stick or slick surface, such as polytetrafluoroethylene, and is designed so that emboli trapped in sac 31 are prevented from passing out of the filter element through the space between guide wire 11 and the lumen of elastomeric cone 34. Cone 34 is sufficiently soft and flexible so that its lumen can expand to permit distal region 12 of guide wire 11 to be pulled proximally through the cone, and then the lumen will seal itself to prevent emboli from escaping through the lumen, as described hereinafter.

Referring now to FIG. 3, preferred methods of using the apparatus of FIG. 1 are described. In FIG. 3A, guide wire 11 first is percutaneously and transluminally inserted into vessel V, such as a coronary artery or common carotid artery, so that distal region 12 is disposed distal of stenosis S in the direction of blood flow (indicated by arrow F).

Figure 3A:
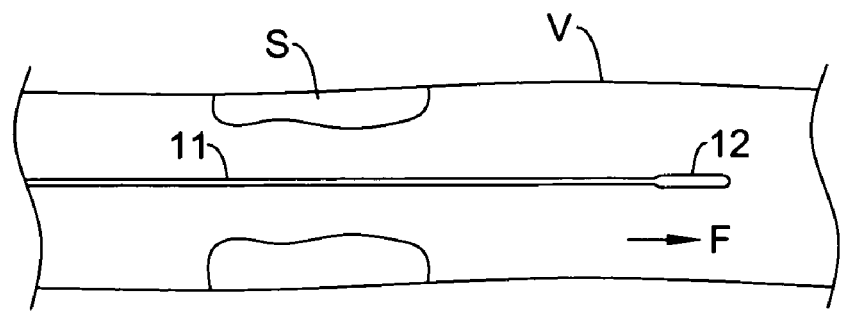
FIGS. 3A-3E are side sectional views showing deployment, use and removal of the apparatus of FIG. 1 in accordance with the methods of the present invention.
Figure 3B:
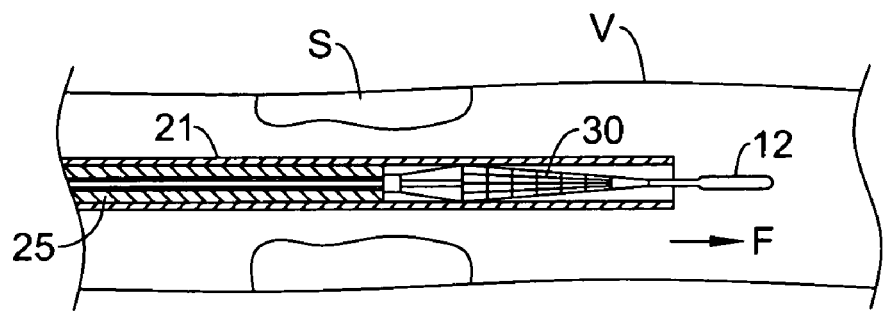

In FIG. 3B, delivery sheath 20 with filter element 30 loaded in lumen 24 in the contracted state is advanced along guide wire 11 until the filter element is disposed at a desired location distal of the stenosis, as determined, for example, by fluoroscopy. Proximal end 26 of push tube 25 is then held stationary while catheter 21 is retracted in the proximal direction.

Figure 3C:
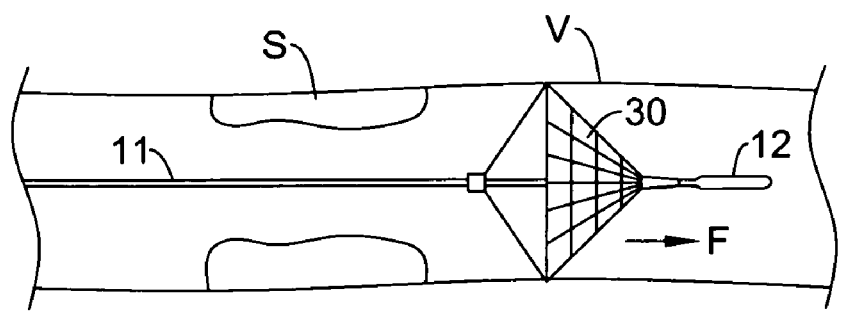

As catheter 21 is retracted, struts 32 of filter element 30 expand outward to urge the perimeter of sac 31 into engagement with the walls of vessel V, as depicted in FIG. 3C. Delivery sheath 20 then is withdrawn proximally and removed from guide wire 11. Guide wire 11 then may be advanced a short distal distally, so that any incidental movement of the guide wire associated with exchanging interventional instruments along guide wire 11 will not cause distal region 12 to contact filter element 30.

Figure 3D:
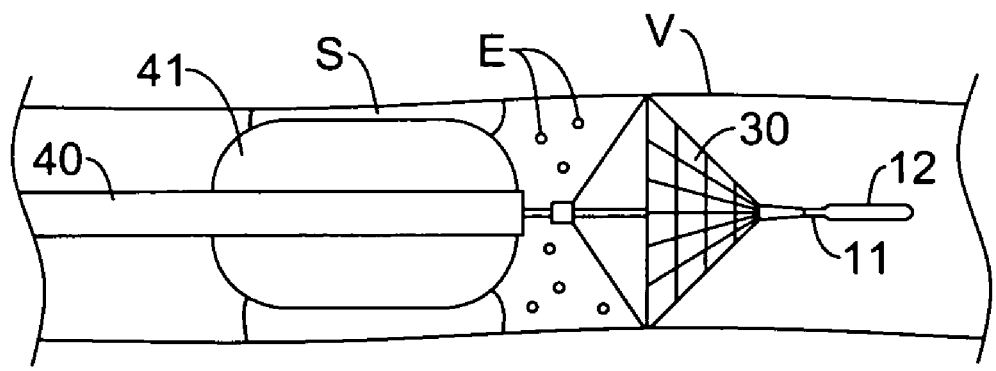
Figure 3E:
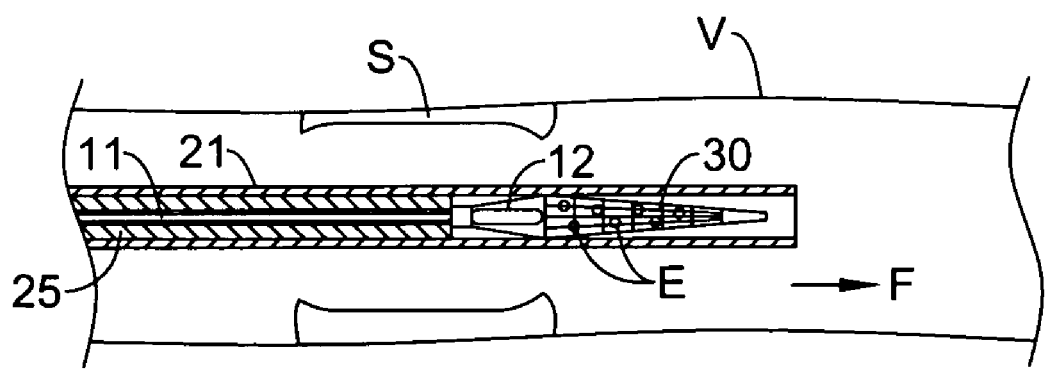

In FIG. 3D, angioplasty catheter 40 is illustratively advanced along guide wire 11 until balloon 41 is disposed across the stenosis. Balloon 41 then is inflated and deflated for one or several cycles, as in conventional, to dilate and disrupt the plaque comprising stenosis S and increase the diameter of vessel V. During this dilatation procedure, particles of plaque or emboli E are generated. These emboli are carried by blood flow in direction F into sac 31 of filter element 30, where they become trapped.

Insertion and advancement of angioplasty catheter 40 along guide wire 11 may cause the guide wire to be translated over a short range or rotated. Because filter element 30 is not affixed to guide wire 11, however, such motion of the guide wire is not transferred to the filter element. Instead, filter element 30 remains stationary even though the guide wire rotates or translates relative to the filter element.

Once balloon 41 has dilated stenosis S, angioplasty catheter 40 is withdrawn along guide wire 11 while leaving the guide wire in place. If desired, a stent delivery system (not shown) may be advanced along guide wire 11 and one or more stents deployed across the dilated stenosis to retain the patency of the dilated vessel.

When treatment of the stenosis is completed, delivery sheath 20 (with push tube 25 removed) may again be advanced along guide wire 11 to a position just proximal of filter element 30. Guide wire 11 then is pulled proximally so that distal region 12 passes through elastomeric cone 34 and bears against capture ring 36. The lumen in cone 34 seals itself after distal region 12 passes through it so that emboli trapped in sac 31 do not escape through the lumen of cone 34.

When guide wire 11 is pulled further in the proximal direction, with catheter 21 held stationary, struts 32 are forced radially inward by the distal edge of the catheter. This in turn causes sac 31 to disengage the vessel walls. As the guide wire continues to be pulled proximally, struts 32 cause sac 31 to collapse inward to its contracted position and the filter element is retracted into lumen 24 of catheter 21. Emboli E are trapped and retained in filter element 30 throughout treatment of the stenosis, and are withdrawn from the vessel when the filter element is retracted within catheter 21. Catheter 21 then is removed from the vessel.

Figure 4A:
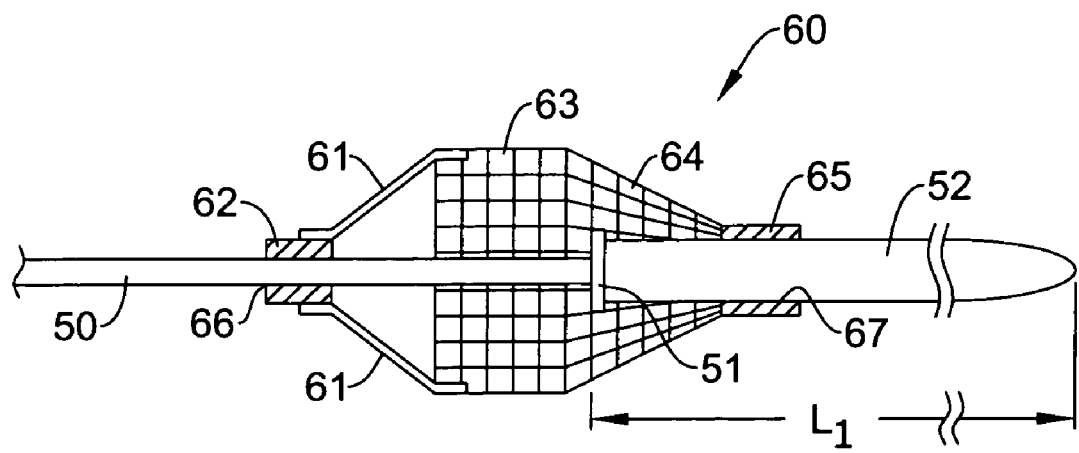
FIGS. 4A-4B are, respectively, side sectional views of an alternative embodiment of the apparatus of the present invention in deployed and contracted states.
Figure 4B:
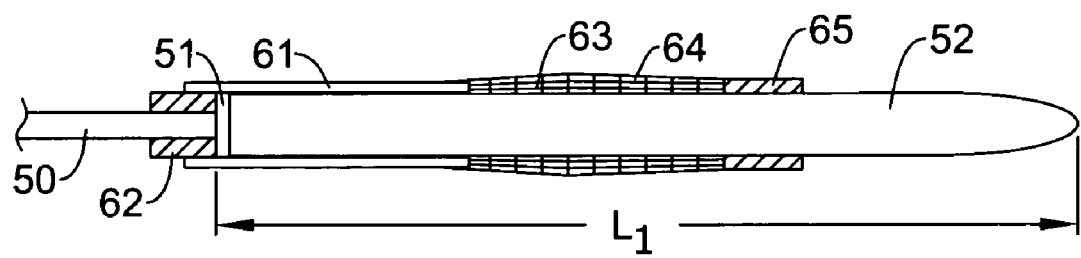

Referring now to FIGS. 4A and 4B, an alternative embodiment of the filter element and guide wire of the present invention is described. Guide wire 50 is similar in construction to guide wire 11 described with respect to FIG. 1, except that it includes flange 51 on enlarged diameter distal region 52 of guide wire 50, and enlarged distal region 52 has length $L_1$ that is longer than the length of the filter element 60 in the contracted state.

Distal region 52 may be formed from a malleable material, a coil spring, or a pliable thermoplastic material molded onto guide wire 50, and preferably is covered with a smooth hydrophilic coating to facilitate movement of filter element 60 as described hereinafter. Alternatively, guide wire 50 and distal region 52 may comprise a mechanism, such as are known in the art, for steering distal region 52 through a patient's vasculature. Distal region 52 also may comprise a radiopaque material or may include a radiopaque band (not shown) to assist in visualization and placement of the guide wire.

Filter element 60 comprises self-expanding struts 61 coupled to capture ring 62 and tubular sleeve 63. Sleeve 63 is affixed at its distal end to funnel-shaped filter sac 64, which in turn is coupled to distal ring 65. Capture ring 62 has bore 66 with an inner diameter larger than the diameter of guide wire 50, but smaller than the diameter of distal region 52. Accordingly, guide wire 50 may freely translate and rotate through bore 66 of capture ring 62 while the filter element remains stationary.

Distal ring 65 has bore 67 with a diameter slightly larger than the diameter of distal region 52. This enables distal ring 65 to slide or rotate freely over distal region 52, but with minimal clearance for emboli to escape from sac 64 through the annulus between distal ring 65 and distal region 52. Distal region 52 includes flange 51, which has a diameter that is larger than the diameter of bore 66 of capture ring 62. Thus, filter element 60 is captured on guide wire 50 proximally by distal ring 65 abutting against flange 51, and distally by capture ring 62 abutting against flange 51.

Sleeve 63 and sac 64 filter blood passing through the vessel, and preferably have a pore size selected to filter out particles having a diameter greater than 0.0012 inches (30 microns). Sleeve 63 and sac 64 preferably comprise a flexible woven metal alloy, polymer tube, or perforated fabric, and are expanded to the deployed state, as shown in FIG. 4A, by struts 61. Advantageously, sleeve 63 is designed so that its perimeter conforms to the inner diameter of the vessel to seal against bypass flow, even in curved vessels. In addition, sleeve 63 tends to prevent skewing of the filter element and ensures that the filter is properly oriented parallel to the axis of the vessel when the filter element is deployed.

Filter element 60 is suitable for delivery percutaneously and transluminally to a desired location in a vessel using delivery sheath 20 of FIG. 1. In particular, struts 61 may be radially compressed to collapse sleeve 63 and sac 64, as shown in FIG. 4B, thereby permitting the filter element to be loaded into lumen 24 of catheter 21 so that capture ring 62 abuts against distal end 27 of push tube 25.

Deployment of filter element 60 is similar to the method described with respect to FIGS. 3B and 3C. Specifically, delivery sheath 20 is advanced through a vessel with distal region 52 extending beyond distal end 23 of catheter 21. Once distal region 52 has crossed the stenosis, as confirmed by fluoroscopy, push tube 25 is held place and catheter 21 is retracted proximally. Alternatively, push tube 25 may be omitted and guide wire 50 may be held stationary with filter element 60 held in position by flange 51. Retraction of catheter 21 uncovers filter element 60, allowing struts 61 to expand outward and urge the perimeter of sleeve 63 and sac 64 into engagement with the walls of the vessel.

Delivery sheath 20 then is removed, and one or more interventional devices may be serially employed on guide wire 50. Like the embodiment of FIG. 1, motion imparted to guide wire 50 during exchange of instruments along the guide wire causes the guide wire to slide through filter element 60 without causing skewing or displacement of the filter element. Advantageously, this prevents emboli from escaping sac 64 or damage to the endothelium caused by scraping of the filter element.

Once treatment of the stenosis is completed, the treatment device (e.g., angioplasty catheter, etc.) is removed, and delivery sheath 20 is again advanced along guide wire 50. When distal end 23 of catheter 21 is disposed adjacent to capture ring 62, guide wire 50 is pulled proximally. As a result of this motion, distal region 52 passes through filter element 60 until flange 51 abuts against capture ring 62. Further proximal movement of guide wire 50 causes struts 61 to be urged inward, collapsing sleeve 63 and sac 64 so that they can be drawn into lumen 24 of catheter 21.

Unlike the embodiment of FIG. 1, where the distal region passes through cone 34, length $L_1$ is sufficiently long so that distal ring 65 is still disposed over the enlarged diameter of distal region 52 when the filter element is in the contracted state. Accordingly, when filter element 60 is contracted for removal, emboli cannot escape through bore 67 of distal ring 65, since the bore continues to be substantially blocked by distal region 52 of guide wire 50. Delivery sheath 20, guide wire 50 and filter element 60 then are removed from the vessel with any emboli trapped within the contracted filter element.

In a preferred embodiment of the apparatus of FIG. 4, guide wire 50 has a suitable length for transluminal percutaneous applications and a diameter in a range of about 0.006 to 0.025 inches, and more preferably 0.012 inches. Distal region 52 of guide wire 50 has a diameter larger than the diameter of guide wire 50, and preferably in a range of about 0.010 to 0.038 inches, more preferably 0.018 inches.

While filter element 60 may comprise any length suitable for an intended application, in one preferred embodiment, filter element 60 has a deployed length of 3.5 cm and a maximum deployed diameter of 12 mm. For this embodiment, length $L_1$ of distal region 52 preferably is 5.0 cm. For a guide wire having a diameter of 0.012 inches and distal region having a diameter of 0.018 inches, capture ring 62 preferably has an inner diameter of 0.014 inches and an outer diameter of 0.018 inches. In this case distal ring 65 preferably has an inner diameter of 0.0181 inches and an outer diameter of 0.024 inches.

Referring now to FIG. 5, apparatus 90 of an alternative embodiment of the present invention comprises guide wire 100 and filter element 102. Filter element 102 preferably is constructed in accordance with filter element 30 of FIGS. 1-3. Specifically, filter element 102 comprises funnel-shaped filter sac 105 coupled to plurality of self-expanding struts 103 at a proximal end and elastomeric cone 106 at a distal end. Struts 103 are affixed to capture ring 104, as described in detail hereinabove with respect to FIG. 2. Optionally, filter element 102 also may comprise cylindrical sleeve 63, as described hereinabove with respect to FIG. 4, disposed between struts 103 and sac 105.

Figure 5A:
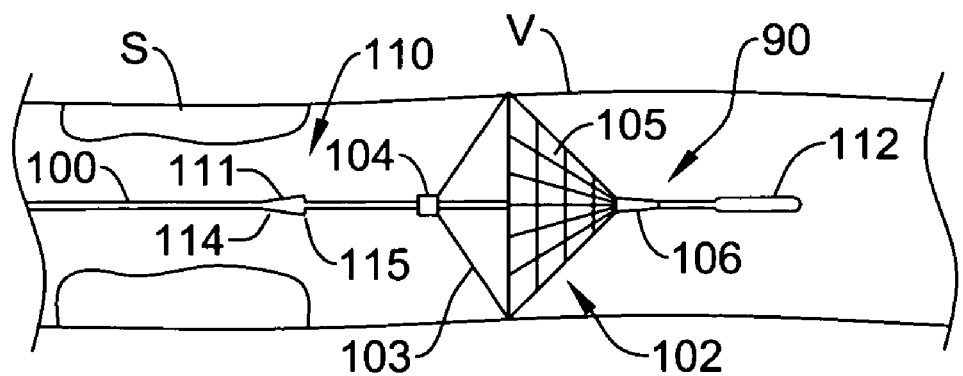
FIGS. 5A-5B are side sectional views depicting use of an alternative embodiment of the present invention having a proximal stop disposed on a guide wire.

Guide wire 100 comprises proximal stop 110 and distal region 112. Distal region 112 serves as a distal stop that limits the distal movement of filter element 102 along guide wire 100, as described hereinabove. Proximal stop 110 has proximal and distal ends 114 and 115 and taper 111 disposed therebetween, as shown in FIG. 5A. Taper 111 of guide wire 110 spans from proximal end 114, which preferably has a guide wire diameter of about 0.018 inches, to distal end 115, which preferably has an enlarged diameter of about 0.022 inches. Proximal stop 110 and distal region 112 are spaced apart such a distance that filter element 102, when deployed therebetween, will not be disturbed by incidental longitudinal movements of guide wire 100.

Apparatus 90 of FIG. 5 preferably is deployed in the manner described hereinabove with respect to apparatus 10 of FIGS. 1-3, except as noted below. In a first step, guide wire 100 is percutaneously and transluminally inserted into treatment vessel V under fluoroscopy, with proximal stop 110 preferably being disposed just distal of stenosis S. In a next step, filter element 102 is advanced along guide wire 100 in a contracted state, preferably being contracted within lumen 24 of catheter 21, as described hereinabove with respect to FIG.

3B. Push tube 25 of FIG. 3B then is advanced distally so that a distal end of push tube 25 abuts capture ring 104 and advances filter element 102 distally over guide wire 100.

As push tube 25 advances filter element 102, elastomeric cone 106 is pushed distally over proximal stop 110 of guide wire 100. Elastomeric cone 106 is configured to be flexible enough to radially expand over the enlarged diameter of distal end 115 of proximal stop 110. After being advanced over distal end 115, elastomeric cone 106 then substantially seals itself about guide wire 100 to prevent emboli from subsequently escaping when a medical procedure is performed.

As push tube 25 further is advanced, capture ring 104 then is advanced over proximal stop 110. Capture ring 104 also is compliant enough to expand over the enlarged diameter of distal end 115 when advanced distally, and then substantially seals itself about guide wire 100 after it passes over proximal stop 110. Once filter element 102 is disposed between proximal stop 110 and distal region 112, filter element 102 is deployed, e.g., by proximally retracting catheter 21 while holding push tube 25 stationary. The catheter and push tube then may be removed from the patient's vessel.

Once deployed, filter element 102 preferably is provided in a central position between proximal stop 110 and distal region 112, as depicted in FIG. 5A, either by proximally retracting or distally advancing guide wire 100 under fluoroscopy. In this central position, incidental movements of guide wire 100 will not substantially disturb filter element 102.

Figure 5B:
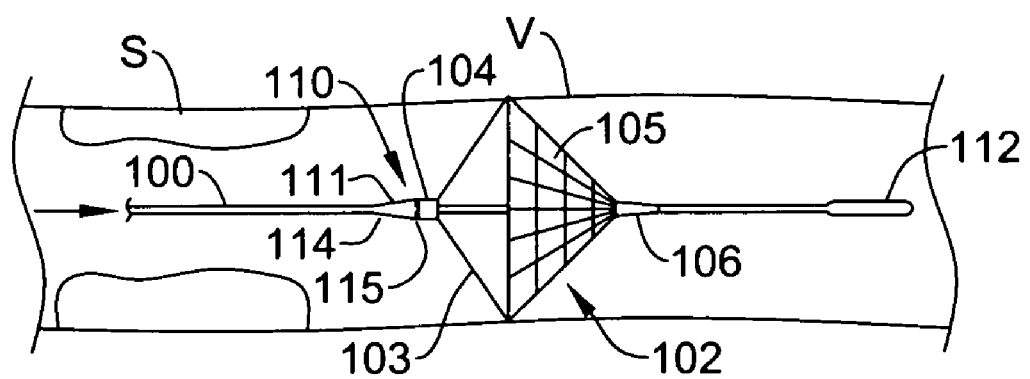

If it becomes necessary to advance filter element 102 distally during the medical procedure, guide wire 100 may be advanced distally by a physician until distal end 115 of proximal stop 110 abuts capture ring 104 and gently urges filter element 102 distally, as shown in FIG. 5B. Advantageously, this enables filter element 102 to be advanced distally without having to remove angioplasty or stenting apparatus, then having to advance a push tube over then length of guide wire 100. Upon repositioning of filter element 102, guide wire 100 preferably is repositioned to the central position depicted in FIG. 5A, so that incidental movements of guide wire 100 do not disturb filter element 102.

When treatment of the stenosis is completed and any emboli are captured within sac 105 of filter element 102, delivery sheath 20 (with push tube 25 removed) may be advanced to a location just proximal of filter element 102. Guide wire 100 then is retracted proximally so that distal region 112 passes through elastomeric cone 106 and bears against capture ring 104, as described hereinabove with respect to FIG. 3E. A lumen of cone 106 seals itself after distal region 112 passes through to prevent emboli from escaping downstream. Distal region 112 then abuts capture ring 104 and pulls filter element 102 in a proximal direction. With the catheter held stationary, struts 103 are forced radially inward by the distal edge of the catheter to cause filter element 102 and any emboli captured therein to be removed via the catheter.

Advantageously, the one-way stop feature of proximal stop 110 allows guide wire 100 to be advanced through a patient's vasculature without having filter element 102 disposed on the guide wire. This facilitates advancement of guide wire 100 through a patient's tortuous vasculature. Then, when guide wire 100 is properly positioned in a vessel unencumbered, filter element 102 may be advanced distally over proximal stop 110, and securely positioned between proximal stop 110 and distal region 112 during the medical procedure.

Figure 6A:
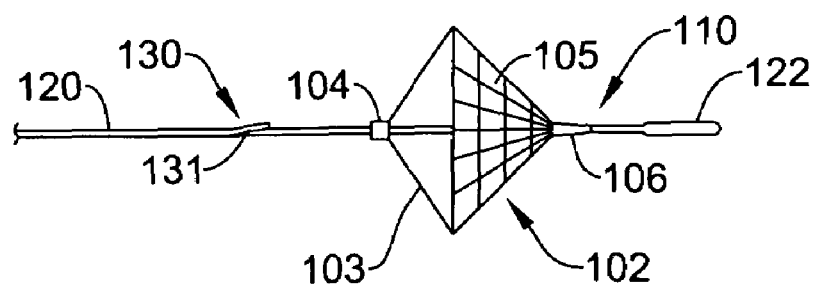
FIGS. 6A-6C are, respectively, a side view of an alternative embodiment of the proximal stop of FIGS. 5A-5B, and enlarged views of the proximal stop in relaxed and contracted states.
Figure 6B:
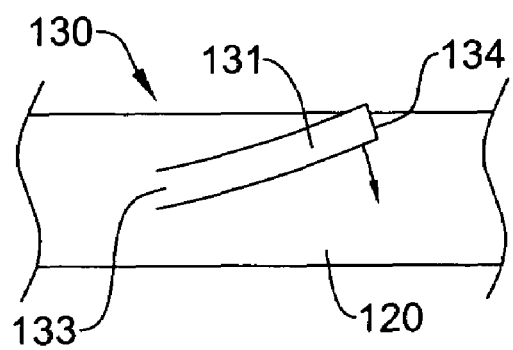
Figure 6C:
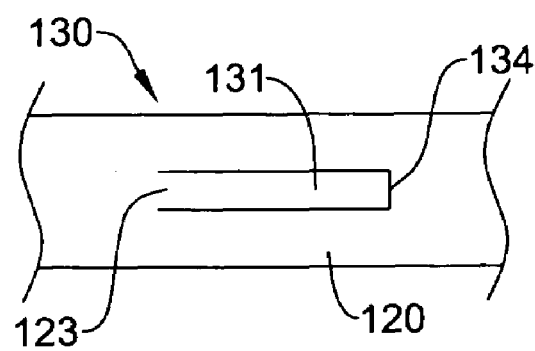

Referring now to FIG. 6, an alternative embodiment of proximal stop 110 of the embodiment of FIG. 5 is described. In FIG. 6A, guide wire 120 preferably is provided substantially in accordance with guide wire 11 of FIG. 1, and comprises enlarged diameter distal region 122, which acts as a distal stop to limit travel of filter element 102 in the distal direction, as described hereinabove. Guide wire 120 further comprises proximal stop 130, which includes at least one depressible tab 131 having proximal end 133 and distal end 134, as shown in FIGS. 6B-6C.

Proximal end 133 of depressible tab 131 is affixed to guide wire 120, e.g., using a solder, while distal end 134 is biased to extend slightly radially outward from guide wire 120 in a relaxed state, as shown in FIG. 6B. Depressible tab 131 may comprise a slight concave curvature to cause distal end 134 to be biased radially outward or, alternatively, proximal end 133 may be affixed to guide wire 120 in such a manner that allows distal end 134 to be biased radially outward in the relaxed state.

Depressible tab 131 is flexible so that it may be transformed between the relaxed state, shown in FIG. 6B, and a contracted state, as shown in FIG. 6C. In the contracted state, external compressive forces cause depressible tab 131 to be substantially flush with an exterior surface of guide wire 120. Guide wire 120 optionally may comprise a shallow slot (not shown) disposed in a lateral surface that is adapted to receive depressible tab 131 in the contracted state. When depressible tab 131 is contracted, as shown in FIG. 6C, the shallow slot serves to ensure that depressible tab 131 does not extend radially beyond guide wire 120.

Apparatus 110 of FIG. 6 preferably is deployed in the manner described hereinabove with respect to apparatus 10 of FIGS. 1-3, except as noted below. In a first step, guide wire 120 is percutaneously and transluminally inserted until proximal stop 130 is disposed just distal of a stenosis. In a next step, filter element 102 is advanced along guide wire 120 in a contracted state, preferably being contracted within lumen 24 of catheter 21, as described hereinabove with respect to FIG. 3B. Push tube 25 of FIG. 3B then is advanced distally so that a distal end of push tube 25 abuts capture ring 104 and advances filter element 102 distally.

As push tube 25 advances filter element 102, elastomeric cone 106 is pushed distally over proximal stop 130. Depressible tab 131 assumes the contracted state, depicted in FIG. 6C, as filter element 102 is advanced distally to facilitate advancement of elastomeric cone 106 over proximal stop 130. Elastomeric cone 106 also may radially expand over proximal stop 130, if necessary, and then substantially seal itself about guide wire 120 after it passes over proximal stop 130. As push tube 25 further is advanced, capture ring 104 then is advanced over proximal stop 130 in the same manner as elastomeric cone 106.

After elastomeric cone 106 and capture ring 104 are advanced distally over proximal stop 130, depressible tab 131 returns to the relaxed state, depicted in FIG. 6B. Filter element 102 then is deployed between proximal stop 130 and distal region 122, e.g., by proximally retracting catheter 21 while holding push tube 25 stationary. The catheter and push tube then may be removed from the patient's vessel.

Once deployed, filter element 102 preferably is provided in a central position between proximal stop 130 and distal region 122 by proximally retracting or distally advancing guide wire 120 under fluoroscopy. If it becomes necessary to advance filter element 102 distally during a medical procedure, guide wire 120 may be advanced distally to cause distal end 134 of depressible tab 131 to abut capture ring 104 and gently urge filter element 102 distally. Upon completion of the medical procedure, catheter 21 may be advanced distally over guide wire 120 to cause filter element 102 and any emboli captured therein to be removed via the catheter, as described in detail hereinabove with respect to FIG. 3E.

Referring now to FIG. 7, a further alternative embodiment of the present invention is described, whereby guide wire 11 of FIG. 1 is slightly bent to comprise a one-way proximal stop mechanism. Guide wire 150 of FIG. 7A comprises enlarged diameter distal region 152, which acts as a distal stop to limit travel of filter element 102 in the distal direction. Guide wire 150 further comprises proximal stop 160, which includes bent section 161 of guide wire 150 having proximal taper 163 and distal taper 164. Proximal taper 163 comprises angle α with respect to longitudinal axis 170 of guide wire 150, while distal taper 164 comprises angle β with respect to longitudinal axis 170, as depicted in FIG. 7B.

Proximal stop 160 is configured to facilitate distal advancement of filter element 102 over bent section 161 of guide wire 150 via proximal taper 163, while inhibiting movement of filter element 102 in a proximal direction over bent section 161 via distal taper 164. In a preferred embodiment, angle β is greater than angle α, as illustratively shown in FIG. 7B, to permit advancement of filter element 102 in a distal direction only.

Proximal stop 160 of guide wire 150 is flexible enough so that proximal and distal tapers 163 and 164 may assume substantially flat configurations, i.e., substantially parallel to longitudinal axis 170 of guide wire 150, when elastomeric cone 106 and capture ring 104 are advanced distally over bent region 161. Once filter element 102 is advanced distally over proximal stop 160, proximal and distal tapers 163 and 164 return to the bent configurations depicted in FIG. 7A.

Apparatus 140 of FIG. 7 preferably is deployed in the manner described hereinabove with respect to apparatus 10 of FIGS. 1-3, except as noted below. In a first step, guide wire 150 is percutaneously and transluminally inserted until proximal stop 160 is disposed just distal of a stenosis. In a next step, filter element 102 is advanced along guide wire 150 in a contracted state, preferably being contracted within lumen 24 of catheter 21, as described hereinabove with respect to FIG. 3B. Push tube 25 of FIG. 3B then is advanced distally so that a distal end of push tube 25 abuts capture ring 104 and advances filter element 102 distally.

As push tube 25 advances filter element 102, elastomeric cone 106 is pushed distally over proximal taper 163 of guide wire 150. Proximal and distal tapers 163 and 164 may assume substantially flat configurations, i.e., substantially parallel to longitudinal axis 170, to facilitate distal advancement of elastomeric cone 106. As push tube 25 further is advanced distally, capture ring 104 then is advanced over proximal stop 160 in the same manner as elastomeric cone 106.

Once filter element 102 is disposed between proximal stop 160 and distal region 152, filter element 102 is deployed, as described hereinabove. Filter element 102 preferably is provided in a central position between proximal stop 160 and distal region 152, as shown in FIG. 7A, by proximally retracting or distally advancing guide wire 150 under fluoroscopy. If it becomes necessary to advance filter element 102 distally during a medical procedure, guide wire 150 may be advanced distally until distal taper 164 of proximal stop 160 abuts capture ring 104 and gently urges filter element 102 distally. Proximal stop 160 of guide wire 150 is configured to retain the bent shape depicted in FIG. 7 as distal taper 164 urges filter element 102 distally. Upon completion of the medical procedure, catheter 21 may be advanced distally over guide wire 150 to cause filter element 102 and any emboli captured therein to be removed via the catheter, as described in detail hereinabove with respect to FIG. 3E.

While preferred illustrative embodiments of the invention are described above, it will be apparent to one skilled in the art that various changes and modifications may be made. The appended claims are intended to cover all such changes and modifications that fall within the true spirit and scope of the invention.

The invention claimed is:

1. An apparatus for filtering emboli from blood flowing through a vessel, the apparatus comprising:
   a guidewire having a distal region and a stop on the distal region;
   a filter element having a proximal coupling slidably coupled to the guidewire proximal of the stop and a distal coupling slidably coupled to the guidewire distal of the stop;
   wherein the stop restricts translation of the filter element along the guidewire; and
   wherein translation of the filter element is restricted on the guidewire proximally by the distal coupling abutting against the stop, and distally by the proximal coupling abutting against the stop.

2. The apparatus of claim 1, wherein the filter element has a range of translation along the guidewire generally determined by the distance between the proximal coupling and the distal coupling.

3. The apparatus of claim 1, wherein the filter element includes a plurality of self-expanding struts coupled to the proximal coupling.

4. The apparatus of claim 1, wherein the filter element includes a filter sac coupled to the distal coupling.

5. An apparatus for filtering emboli from blood flowing through a vessel, the apparatus comprising:
   a guidewire having a diameter and a distal region;
   a filter element including a proximal ring slidably coupled to the guidewire and a distal ring slidably coupled to the guidewire, the proximal ring having a bore greater than the diameter of the guidewire and the distal ring having a bore greater than the diameter of the guidewire;
   a stop disposed on the distal region of the guidewire intermediate the proximal ring and the distal ring;
   wherein stop has a diameter greater than the bore of the proximal ring;
   wherein the stop has a diameter greater than the bore of the distal ring; and
   wherein translation of the filter element is restricted on the guidewire proximally by the distal ring abutting against the stop, and distally by the proximal ring abutting against the stop.

6. The apparatus of claim 5, wherein the guidewire includes a distal region having an enlarged diameter, wherein the enlarged diameter is greater than the bore of the proximal ring and is less than the bore of the distal ring.

7. The apparatus of claim 5, wherein the guidewire includes a distal region having an enlarged diameter, wherein the stop is greater than the enlarged diameter of the distal region.

8. The apparatus of claim 5, wherein the filter element includes a plurality of self-expanding struts coupled to the proximal ring and a filter sac coupled to the distal ring.

9. The apparatus of claim 5, wherein the filter element has a contracted state suitable for transluminal delivery, and the guidewire includes a distal region distal of the stop having a length greater than a length of the filter element in the contracted state.

* * * * *